(12) United States Patent
Bloore et al.

(10) Patent No.: US 6,910,885 B2
(45) Date of Patent: Jun. 28, 2005

(54) TWIST ON ORTHODONTIC HOOK

(76) Inventors: John A. Bloore, 808 Franklin St., Santa Monica, CA (US) 90403; Glenn E. Bloore, 300 S. Beverly Dr. #101, Beverly Hills, CA (US) 90212

( * ) Notice: Subject to any disclaimer, the term of this patent is extended or adjusted under 35 U.S.C. 154(b) by 0 days.

(21) Appl. No.: 10/632,506

(22) Filed: Aug. 4, 2003

(65) Prior Publication Data

US 2005/0032016 A1 Feb. 10, 2005

(51) Int. Cl.[7] .................................................. A61C 7/00
(52) U.S. Cl. ........................................... 433/15; 433/19
(58) Field of Search .......................... 433/3, 4, 10, 11, 433/20, 15, 19, 22

(56) References Cited

U.S. PATENT DOCUMENTS

| 4,522,590 A | * | 6/1985 | Pletcher | 433/15 |
| 5,018,969 A | * | 5/1991 | Andreiko et al. | 433/20 |
| 5,885,074 A | * | 3/1999 | Hanson | 433/13 |

OTHER PUBLICATIONS

OIS catalog www.oisortho.com catalog page titled Treatment Auxiliaries.

* cited by examiner

*Primary Examiner*—Cary E. O'Connor

(57) ABSTRACT

An attachable orthodontic hook for use on an orthodontic appliance wherein the hook is formed from a continuous wire which forms a twisted hook when it is attached to an orthodontic appliance. When installed there is only one end. The cut pigtail has been eliminated.

8 Claims, 3 Drawing Sheets

TWIST ON ORTHODONTIC HOOK

FIELD OF THE INVENTION

This invention relates, in general, to an improved orthodontic device, and more particularly to an orthodontic assembly which is attached to an orthodontic bracket, forming an orthodontic hook. More particularly, the orthodontic assembly is constructed from a continuous wire and attached to an orthodontic bracket in a manner that a pigtail hook projects from the orthodontic bracket.

BACKGROUND OF THE INVENTION

The orthodontic procedures for straightening teeth today involves the placement of brackets on the external of the teeth with an adhesive and connecting a force, an arch wire, to the brackets to move the teeth. Hooks have been secured to the brackets and arch wires for use as an anchoring device for intramaxillary or intermaxillary springs, elastomeric modules, elastics, or ligature wires. In the treatment of dentofacial deformities where orthognathic surgery has moved one or both jaws the jaws are often postoperatively ligated together using intermaxillary ligature wires tied to orthodontic hooks to immobilize the jaws, allowing healing in the new position.

Hooks have been secured to arch wires by welding or silver soldering as described in U.S. Pat. No. 3,508,332 at column 1, lines 35 and 36. If the manufacturer places the hooks it is difficult for the hooks to be attached to an arch at locations best suited for a particular patient. A great amount of skill is required of the orthodontist to place the hooks on an arch wire without inadvertently annealing the arch wire. An arch which becomes annealed loses Its ability to transmit orthodontic forces effectively to the teeth to which the brackets carrying the arch are bonded. The movement of soldered or electro-welded arch wires hooks which have been in the mouth is further complicated by the fact the wire must be absolutely clean in order to place a new hook. Cleanliness is difficult to assure for an arch wire that has been in the mouth any appreciable length of time.

Alternately, hooks have been mounted on caps engageable with orthodontic brackets, as described in U.S. Pat No. 3,391,461 at column 2, lines 24 and 25. A principal difficulty with such a hook mounting is that it is necessary to hold the cap in place on the bracket while bending the retaining tabs to engage the bracket, which also may exert force on the bracket. Bending of the tabs to remove the hook mounting may additionally exert force on the bracket.

Hooks have been attached to arch wires by small set screws as found in U.S. Pat. No. 3,158,934 and U.S. Pat. No. 4,639,219. The set screws tend to loosen in the mouth.

Another method has been to crimp the hook to the arch using a crimping tool. Even when the hooks are crimped they tend to slide along the arch wire.

In U.S. Pat. No. 4,797,095 an intricate removable hook attaches to the arch wire where it also embraces the bracket.

The hook which most resembles the present invention is the Kobyashi tie wire which is a ligature tie wire, usually 0.012 inches in size, tack welded approximately 4 mm from its closed end. The closed-end forms a hook as it is tied as a normal ligature wire. The tied end forms a pigtail which has to be cut and pushed under the arch wire for patient comfort. The tucking of the pigtail often loosens the hook and the cut end often is bent towards the patient's cheek or lip and pokes the patent while being worm.

Recently hooks have been manufactured as an integral part of the orthodontic bracket. The disadvantage of this type of hook is the orthodontist must predict the locations hooks will be needed during treatment at the time the braces are installed. The need for hooks in certain areas usually develops during treatment and initially placing hooks everywhere may be more uncomfortable for the patient along with more difficult oral hygiene.

SUMMARY OF THE INVENTION

The present invention is directed to an orthodontic hook attached to an orthodontic appliance for the attachment of a elastics, elastomeric modules, springs, cables, and ligature wires. Specifically the invention is designed to be attached to an orthodontic bracket producing a hook and, most importantly, the absence of a ligature end which must be cut and tucked in. A further object of the orthodontic hook is ease of installation, no special mounting to the orthodontic bracket or welding or soldering to the orthodontic arch wire is required. Another object is to provide a mounting which is strong and retained in place securely. An additional object is to provide a hook which can be Installed on the orthodontic appliance in any chosen position. A final object is easy removal of the hook; it is removed as easily as a ligature be wire.

The orthodontic hook is comprised of a continuous orthodontic wire with a perimeter. The dimension of the wire perimeter is determined by the amount of wire required to be secured to the wings of an orthodontic bracket and to form a 3 mm to 6 mm length hook. The wire is formed to be continuous. The continuous wire can be manufactured continuous or the wire ends can be joined by processes such as micro soldering, soldering, micro welding, or welding.

In a preferred embodiment the orthodontic hook is constructed of 0.010 inch to 0.014 inch diameter wire in a circular form approximately 4 mm to 10 mm in diameter. The diameter of the circle varies according to the differing sizes and shapes of orthodontic bracket wings. For example, a twin bracket would require a larger perimeter wire than a single bracket. The tie hook is formed by gripping a small section of the circular wire with a pair of pliers, preferably locking pliers, and engaging the bracket wings while positioning the plier-held section of the wire in the position of the future tie hook. The pliers are rotated in their long axis until the bracket wings are firmly engaged by the wire and a pigtail hook is formed.

In an alternative embodiment of the present invention the tie wire is oval with the same size range as the circular wire.

In another embodiment of the present invention the be wire is rectangular in shape, with the width of the rectangle sufficient to fit over the tie wings of a bracket. At one end of a side of the rectangle the wire extends outwardly in the longitudinal direction the rectangle to form a small tab. The tab is gripped by the pliers and is the future location of the pigtail hook.

In a further embodiment the arch wire hook may be formed from multiple wires pigtailed or braided into a 0.10 in to 0.014 in diameter.

DETAILED DESCRIPTION THE INVENTION

Figures 1, 2, 3, 4:
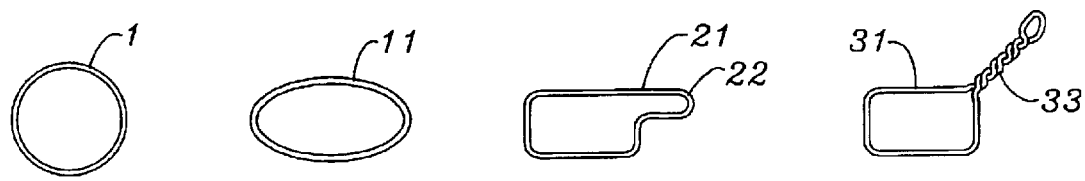
FIG. 1 is a view of the orthodontic hook.
FIG. 2 is a view of the second embodiment of the orthodontic hook.
FIG. 3 is a view of another embodiment of the orthodontic hook.
FIG. 4 is a view of the orthodontic hook after installation.
Figure 5:
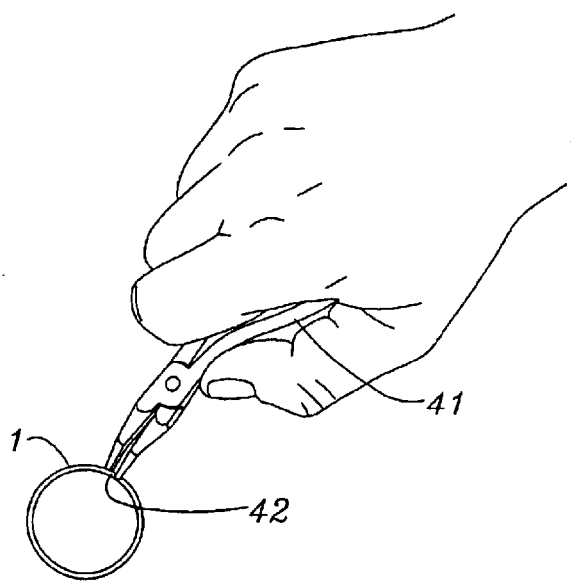
FIG. 5 is a view of the orthodontic hook prior to installation.
Figure 6:
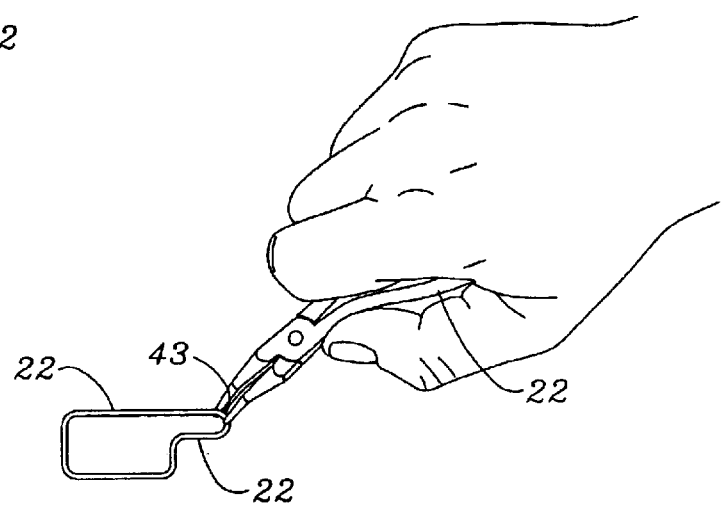
FIG. 6 is a view of the orthodontic hook In another embodiment prior to installation.
Figure 7:
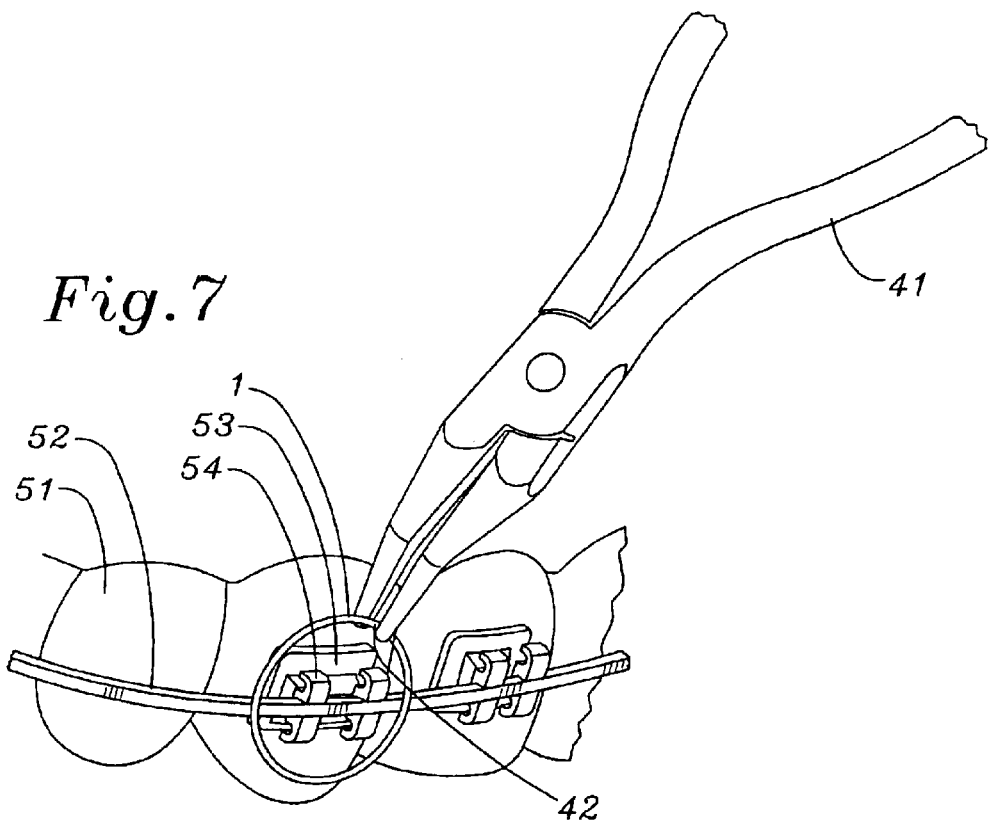
FIG. 7 is a prospective view of the orthodontic hook being installed.
Figure 8:
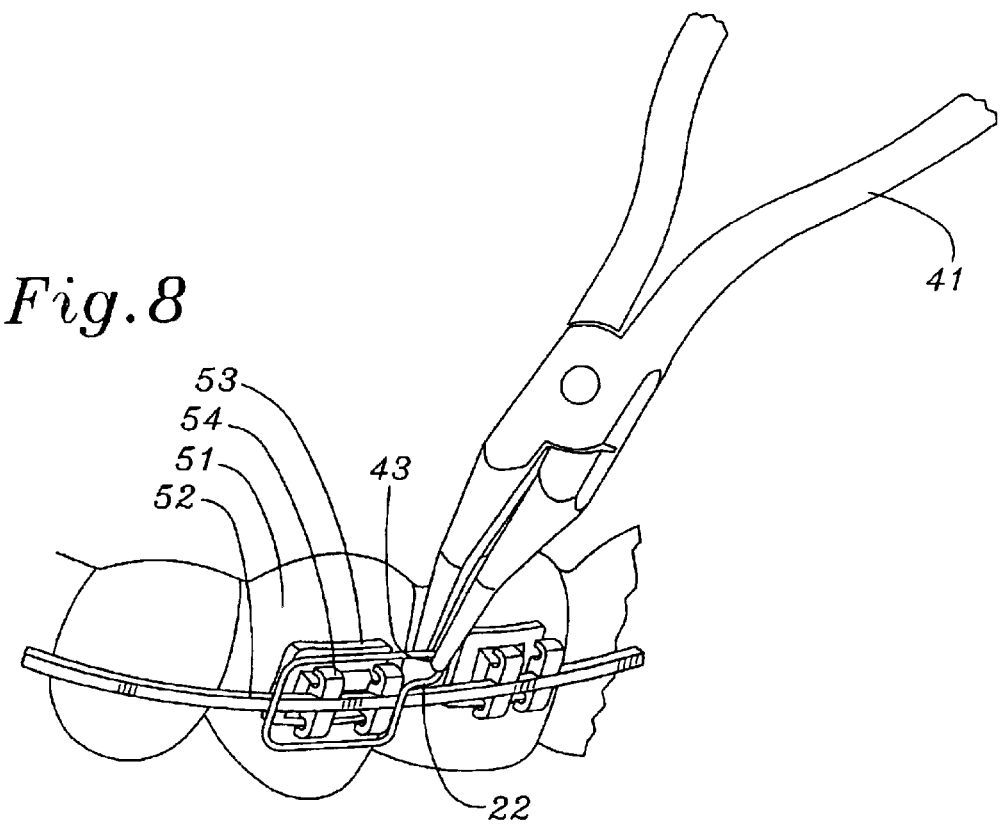
FIG. 8 is a prospective view of another embodiment of the orthodontic hook being installed.
Figure 9:
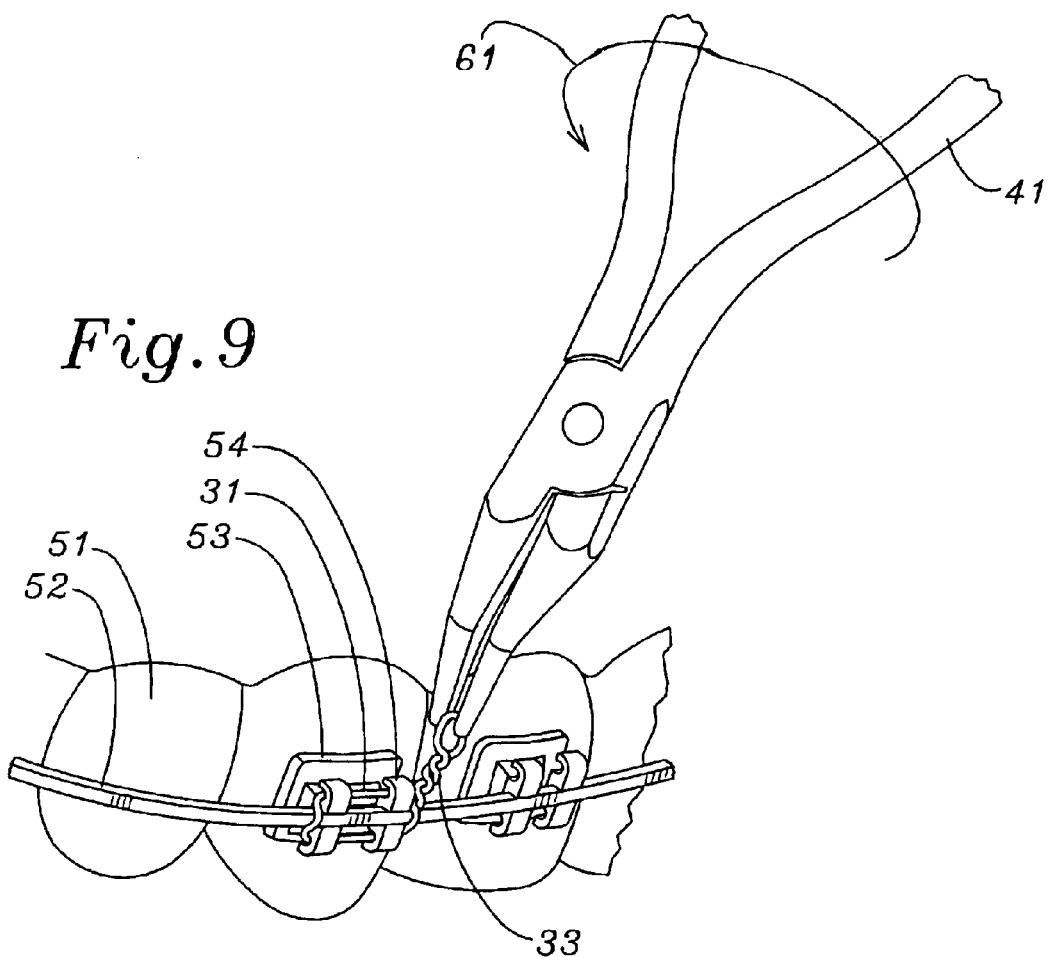
FIG. 9 is a prospective view of the orthodontic hook after the installation on the orthodontic bracket is complete.
Figure 10:
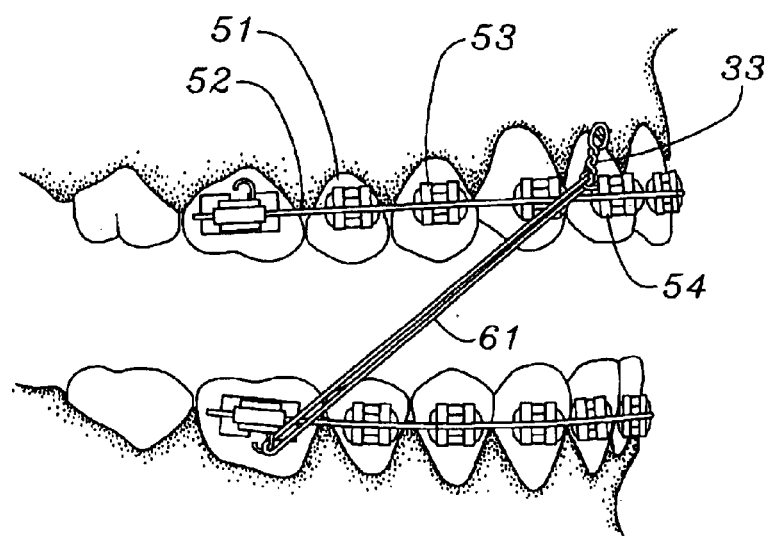
FIG. 10 is a side view of an orthodontic appliance in the mouth with the orthodontic hook being used for intermaxillary elastics.

Referring to FIGS. 1–3, the orthodontic hook 1 is constructed for installation on a conventional orthodontic assembly of an arch wire 52 attached to brackets 53 which are attached to the front faces of teeth 51, as shown FIGS. 7–10. Each tooth bracket 53 includes a base 55 bonded to the outer surface of a tooth 51. A body projects outwards from the bracket base 55 and carries a plurality of wings 54 projecting upwards and downwards from the opposite side of a groove or slot 56 between them in which the arch wire 52 is fitted. Normally the arch wire 52 is tied to each bracket 53 by an elastomeric ring or a fine wire as shown in FIGS. 7, 8, and 10. In FIGS. 7, 9, and 10 the orthodontic hook 1 is tied to the bracket tie wings 54 either under the arch wire 52 or over the arch wire 52, securing the arch wire 52. The orthodontic hook 1 is installed on the bracket assembly virtually any location around the dental arch.

The orthodontic hook 1 may be made from various types of alloys which include: stainless steel, chrome-cobalt alloys, elgiloy (chrome-cobalt-nickel alloys), nickel-cobalt alloys, gold alloys (65_Au-5_Pt-2_Pd-15_Cu-10_Ag), Nidnol (55_Ni-45_Ti), beta-titanium (79_Ti-11_Mo-6_Zr-4_Sn), and numerous other compositions. Wire used for the orthodontic hook 1 is best annealed (soft tempered) to allow workability and to eliminate any wire memory. The orthodontic hook 1 is formed from a single standed wire with a diameter of 0.08 inch to 0.014 inch. The orthodontic hook 1 may also be formed from two or more braided or twisted wires with a collective diameter of 0.08 inch to 0.014 inch.

The orthodontic hook 1 can be a variety of shapes, consequently the shape shown in the drawings should be considered barely representative. Three differently shaped orthodontic hooks 1 are depicted in FIGS. 1–3. The differently shaped orthodontic hooks 1 all have an important common characteristic, the wire is continuous. The wire may be constructed continuous, for example, by slicing a metal tube; or the ends may be joined by micro welding, micro soldering, electro welding or soldering. In FIG. 1 the orthodontic hook 1 is circular 2. The diameter of the circle is determined by the amount of wire necessary to ligate an orthodontic bracket 63 and to produce a pigtail hook 33 4 mm to 10 mm long, as shown In FIG. 4. The diameter of the circular wire 2 will vary depending upon the different sizes and shapes of orthodontic brackets 53. The orthodontic hook 1 produced with this invention is novel because there is no cut tie end. The prior art tied hooks, such as the Kobyashi hook, resulted in a cut pigtail tie end which tends to loosen the attachment when the cut end is pushed in, and the cut end tends to move during patient use.

FIG. 2 is another embodiment wherein the orthodontic hook 1 is oval 11. The circumference of the oval wire 11 corresponds to the circular wire 2.

FIG. 3 is another embodiment wherein the wire is formed in a rectangle 21 with a tab 22. The width of the rectangle 21 should be sufficient to place over the upper and lower wings 54 of the orthodontic bracket 53. A side of the of the rectangle extends at one end to form a tab 22 which will form the pigtail hook 33 after Installation, as shown in FIG. 4. The circumference of the rectangular wire 21 is the same as the circular wire 2 in FIG. 1.

The orthodontic hook 1 is formed by gripping the wire with a pair of pliers 4, as shown in FIGS. 5–9, engaging the bracket wings 54, and rotating the pliers 41, FIG. 9, axially until the orthodontic bracket 53 is firmly gripped and the pigtail hook 33 is formed.

In FIG. 10 an orthodontic appliance is depicted with class 2 elastics 61 attached from a molar hook to an orthodontic hook 1. Elastomeric modules, intermaxillary cables, and intermaxillary springs may be attached in a similar manner. Additionally, ligature wires may be tied between the jaws, using the orthodontic hooks 1, to immobilize a Jaw following orthognathic surgery until the jaw is stable.

The invention has been described with specific embodiments, however, the intent of the invention is to provide an orthodontic hook which is comprised of a hook end and is free from having another end which was used for tying and must be cut and pushed under the arch wire. It will be understood that modification and variations may be effected without departing from the scope of the novel concepts of the present invention, but is understood this application is to be limited only by the scope of the appended claims.

What is claimed:

1. A tie on orthodontic hook for attaching to brackets of an orthodontic appliance to be used for the attachment of elastics and other orthodontic devices comprising:

a continuous planar wire with a circular cross section;

a rectangular shaped portion of the continuous planar wire; and a planar tab portion of wire continuous with the rectangular-shaped portion wherein the tab portion extends outwards from the rectangular-shaped portion whereby the orthodontic hook is formed by gripping the planar tab portion with a pair of pliers, placing the circular body over the orthodontic tie wing, engaging the orthodontic wings with the circular body, and rotating the pliers in their axial direction until the circular body engages the orthodontic tie wing and the orthodontic hook is formed from the planar tab portion.

2. A tie on orthodontic hook as in claim 1 wherein the cross-sectional diameter of the rectangular shaped body wire and continuous tab wire is 0.008 inch to 0.014 inch.

3. A tie on orthodontic hook as in claim 1 wherein the rectangular shaped body wire and continuous tab wire is a single strand.

4. A tie on orthodontic hook as in claim 1 wherein the wherein the rectangular shaped body wire and continuous tab wire is multiple strand of two or more wires with a combined diameter of 0.008 inch to 0.014 inch.

5. A tie on orthodontic hook for attaching to brackets of an orthodontic appliance to be used for the attachment of elastics and other orthodontic devices comprising:

a continuous planar wire body with a rectangular cross section;

a determinable body circumference wherein the circumference is determined by an orthodontic bracket size and a hook size desired;

a rectangular shaped portion of the continuous planar wire; and a tab portion of the continuous planar wire continuous with the rectangular-shaped portion wherein the tab portion extends outwards from the rectangular-shaped portion whereby the orthodontic hook is formed by gripping the planar tab portion with a pair of pliers, placing the circular body over the orthodontic tie wing, engaging the orthodontic wings with the circular body, and rotating the pliers in their axial direction until the circular body engages the orthodontic tie wing and the orthodontic hook is formed from the planar tab portion.

6. A tie on orthodontic hook as in claim 5 wherein the diameter of the wire is 0.008 inch to 0.014 inch.

7. A tie on orthodontic hook as in claim 5 wherein the wire is a single strand.

8. A tie on orthodontic hook as in claim 5 wherein the wire is multiple strand of two or more wires with a combined diameter of 0.008 inch to 0.014 inch.

\* \* \* \* \*